United States Patent
Grimm et al.

(10) Patent No.: US 7,002,021 B2
(45) Date of Patent: Feb. 21, 2006

(54) DIKETOPYRROLOPYRROLE PIGMENTS

(75) Inventors: Felix W. Grimm, Hofheim (DE); Hans Joachim Metz, Darmstadt (DE); Joachim Weber, Frankfurt am Main (DE); Andreas Wacker, Mannheim (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 10/520,838

(22) PCT Filed: Jun. 6, 2003

(86) PCT No.: PCT/EP03/05968
§ 371 (c)(1),
(2), (4) Date: Jan. 7, 2005

(87) PCT Pub. No.: WO2004/007500
PCT Pub. Date: Jan. 22, 2004

(65) Prior Publication Data
US 2005/0234243 A1  Oct. 20, 2005

(30) Foreign Application Priority Data
Jul. 10, 2002 (DE) .................. 102 31 105

(51) Int. Cl.
C09B 57/00 (2006.01)
C07D 235/26 (2006.01)
C07D 403/04 (2006.01)
C09D 11/00 (2006.01)
C08K 5/3447 (2006.01)

(52) U.S. Cl. ............. 548/305.4; 548/306.1; 548/306.4; 524/93; 106/31.78; 106/494; 106/498

(58) Field of Classification Search ............ 548/305.4, 548/306.1, 306.4; 524/93; 106/31.78, 494, 106/498
See application file for complete search history.

(56) References Cited

U.S. PATENT DOCUMENTS

| 4,415,685 | A | 11/1983 | Iqbal et al. |
| 4,490,542 | A | 12/1984 | Iqbal et al. |
| 4,579,949 | A | 4/1986 | Rochat et al. |
| 4,585,878 | A | 4/1986 | Jost et al. |
| 4,613,669 | A | 9/1986 | Cassar et al. |
| 4,666,455 | A | 5/1987 | Jost et al. |
| 4,931,566 | A | * 6/1990 | Surber et al. ........ 548/453 |
| 5,560,760 | A | 10/1996 | Toeppen |
| 5,817,832 | A | 10/1998 | Wallquist et al. |
| 6,207,697 | B1 | 3/2001 | Han et al. |
| 6,566,519 | B1 | 5/2003 | Nickel et al. |
| 6,723,138 | B1 | 4/2004 | Nickel et al. |

FOREIGN PATENT DOCUMENTS

| EP | 0061426 | 9/1982 |
| EP | 0094911 | 11/1983 |
| EP | 0098808 | 1/1984 |
| EP | 0133156 | 2/1985 |
| EP | 0755933 | 1/1997 |
| WO | WO 0034248 | 6/2000 |

OTHER PUBLICATIONS

PCT ISR for PCT/EP 03/05968, Sep. 24, 2003.
English Translation of PCT IPER for PCT/EP 03/05968, mailed Mar. 20, 2005.

* cited by examiner

Primary Examiner—Fiona T. Powers
(74) Attorney, Agent, or Firm—Anthony A. Bisulca

(57) ABSTRACT

Diketopyrrolopyrroles of the formula (I):

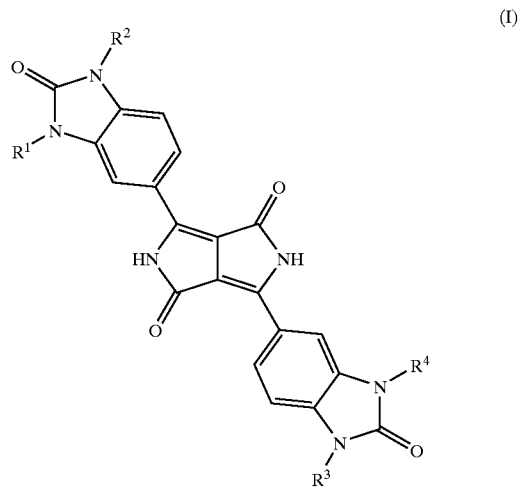

wherein
$R^1$, $R^2$, $R^3$ and $R^4$ independently of one another are a $C_1$–$C_4$ alkyl radical or a substituted or unsubstituted phenyl radical, wherein the phenyl radical can be substituted by 1, 2, 3 or 4 substituents from the group $C_1$–$C_4$ alkyl, $C_1$–$C_4$ alkoxy, CN, F, Cl, Br, $NO_2$, $CF_3$, S—$C_1$–$C_4$ alkyl, phenyl or ($C_1$–$C_2$) alkylenephenyl,
with the proviso that at least one of the radicals, $R^1$, $R^2$, $R^3$, or $R^4$, is one of the stated substituted or unsubstituted phenyl radicals.

12 Claims, No Drawings

DIKETOPYRROLOPYRROLE PIGMENTS

The present invention relates to new 1,4-diketopyrrolo[3,4-c]pyrroles, referred to below as diketopyrrolopyrroles, which constitute valuable pigments, and also to their preparation and use for pigmenting high molecular mass materials.

EP-A-0 061 426 discloses a process for the bulk coloring of high molecular mass organic material, characterized by the use of a diketopyrrolopyrrole.

EP-A-0 094 911 discloses a process for preparing diketopyrrolopyrroles.

The use of pigments for coloring high molecular mass organic materials imposes exacting requirements on the performance properties of the pigments, such as high color strength, effective light fastness and weather fastness, excellent overcoating fastnesses in the case of use in coating systems, low viscosity of the highly pigmented paint concentrates (millbase) and, particularly in the case of metallic finishes, high transparency and brilliant colors. In the case of the coloring of plastics there is a demand for effective dispersibility, which is manifested, for example, in high color strengths. In printing systems, too, high color strengths are a requirement. The pigments ought to be useful as universally as possible.

Many of the diketopyrrolopyrroles disclosed in the above-mentioned publications, however, no longer satisfy present-day requirements.

It was therefore an object to find new diketopyrrolopyrrole pigments which in comparison with the existing diketopyrrolopyrrole pigments possess superior properties.

It has been found that this object, surprisingly, is achieved by means of diketopyrrolopyrrole pigments defined below.

The invention provides diketopyrrolopyrroles of the formula (I),

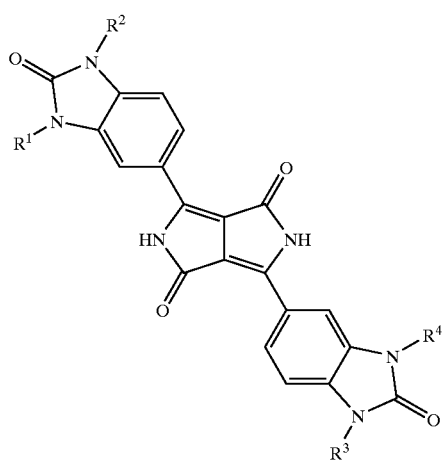

(I)

in which
$R^1$, $R^2$, $R^3$ and $R^4$ independently of one another are a $C_1$–$C_4$ alkyl radical or a substituted or unsubstituted phenyl radical, it being possible for the phenyl radical to be substituted by 1, 2, 3 or 4 substituents from the group $C_1$–$C_4$ alkyl, $C_1$–$C_4$ alkoxy, CN, F, Cl, Br, $NO_2$, $CF_3$, S—$C_1$–$C_4$ alkyl, phenyl or ($C_1$–$C_2$)alkylenephenyl, with the proviso that at least one of the radicals, $R^1$, $R^2$, $R^3$ or $R^4$, is one of the stated substituted or unsubstituted phenyl radicals.

The present invention also provides mixtures of two or more, such as 2 or 3, diketopyrrolopyrroles of the formula (I).

Preferably $R^1$, $R^2$, $R^3$ and $R^4$ independently of one another are methyl, ethyl, phenyl or else phenyl substituted by 1 or 2 substituents from the group methyl, ethyl, methoxy, ethoxy, CN, F, Cl, S-methyl, phenyl or benzyl.

Of particular interest are symmetrical diketopyrrolopyrroles of the formula (I), in which $R^1$ and $R^4$ are identical and $R^2$ and $R^3$ are identical, especially diketopyrrolopyrroles of the formula (I) in which $R^1$ and $R^4$ are each a methyl or ethyl group and $R^2$ and $R^3$ are identical and are each a phenyl radical which is unsubstituted or substituted by 1 or 2 substituents from the group methyl, ethyl, methoxy, ethoxy, F, Cl, $NO_2$, $CF_3$, phenyl or benzyl.

The diketopyrrolopyrrole pigments of the invention and the mixtures according to the invention can be prepared by reacting a succinic diester with a nitrile of the formula (II) or (III),

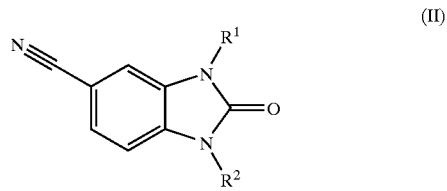

(II)

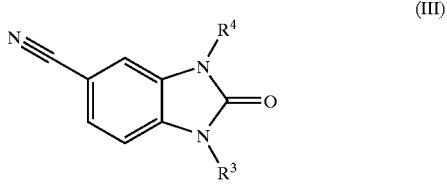

(III)

or with a mixture of 2, 3 or 4 different nitrites of the formula (II) or (III), in an organic solvent in the presence of a strong base with subsequent hydrolysis, where $R^1$ to $R^4$ are as defined above.

The succinic diesters to be used can be dialkyl, diaryl or monoalkyl monoaryl esters and the succinic dialkyl esters and diaryl esters may also be asymmetric. Preference is given to using symmetrical succinic diesters, especially symmetrical succinic dialkyl esters. If the ester is a succinic diaryl ester or succinic monoaryl monoalkyl ester, then aryl denotes, in particular, phenyl which is unsubstituted or substituted by 1, 2 or 3 substituents from the group halogen, such as chloro, $C_1$–$C_6$ alkyl, such as methyl, ethyl, isopropyl, tert-butyl or tert-amyl, or $C_1$–$C_6$ alkoxy, such as methoxy or ethoxy. Aryl is preferably unsubstituted phenyl. Where the ester is a succinic dialkyl ester or succinic monoalkyl monoaryl ester, alkyl can be unbranched, branched or cyclic, preferably branched, and contain preferably 1 to 18, in particular 1 to 12, especially 1 to 8 and with particular preference 1 to 5 carbon atoms. Alkyl is preferably sec- or tert-alkyl, such as isopropyl, sec-butyl, tert-butyl, tert-amyl, cyclohexyl, heptyl, 2,2-dimethylhexyl, octyl, decyl, dodecyl, tetradecyl or octadecyl, for example.

Examples of succinic diesters are dimethyl, diethyl, dipropyl, dibutyl, dipentyl, dihexyl, diheptyl, dioctyl, diisopropyl, di-sec-butyl, di-tert-butyl, di-tert-amyl, di[1,1-dimethylbutyl], di[1,1,3,3-tetramethylbutyl], di[1,1-dimethylpentyl], di[1-methyl-1-ethylbutyl], di[1,1-diethylpropyl], diphenyl, di[4-methylphenyl], di[2-methylphenyl], di[4-chlorophenyl], di[2,4-dichlorophenyl], monoethyl monophenyl or dicyclohexyl succinate.

Use is made in particular of symmetrical succinic dialkyl esters in which alkyl is branched and contains 3 to 5 carbon atoms.

The succinic diesters and the nitriles are known compounds and can be prepared by known processes.

The amount of the nitrile used or the total amount of the nitriles used ought to be stoichiometric with respect to the amount of succinic diester, in other words 2 mol of nitrile per mole of succinic diester. It has nevertheless proven advantageous to use an excess of nitrile or of succinic diester in order to obtain higher yields. Advantageously, relative to the stoichiometric amounts, excesses of nitrile or of succinic diester of up to 10 times are used, preferably up to 5 times, in particular up to 3 times. Excess nitrile can be recovered.

The reaction of the succinic diester with the nitrile is carried out in an organic solvent. Examples of suitable solvents include primary, secondary or tertiary alcohols having 1 to 10 carbon atoms, such as methanol, ethanol, n-propanol, isopropanol, n-butanol, sec-butanol, tert-butanol, pentanols, such as n-pentanol or 2-methyl-2-butanol, hexanol, such as 2-methyl-2-pentanol or 3-methyl-3-pentanol, 2-methyl-2-hexanol, 3-ethyl-3-pentanol, octanols, such as 2,4,4-trimethyl-2-pentanol, cyclohexanol, or glycols, such as ethylene glycol, diethylene glycol, propylene glycol, dipropylene glycol or glycerol, or polyglycols, such as polyethylene glycols or polypropylene glycols, ethers, such as methyl isobutyl ether, tetrahydrofuran, dimethoxyethane or dioxane, glycol ethers, such as monomethyl or monoethyl ethers of ethylene glycol or of propylene glycol, diethylene glycol monomethyl ether or diethylene glycol monoethyl ether, butyl glycols or methoxybutanol, dipolar aprotic solvents, examples being acid amides such as dimethylformamide, N,N-dimethylacetamide or N-methylpyrrolidone, urea derivatives such as tetramethyl urea, aliphatic or aromatic hydrocarbons, such as cyclohexane or benzene or alkyl-, alkoxy-, nitro- or halogen-substituted benzene, such as toluene, xylenes, ethylbenzene, anisole, nitrobenzene, chlorobenzene, o-dichlorobenzene or 1,2,4-trichlorobenzene, aromatic N-heterocycles, such as pyridine, picoline or quinoline, and also hexamethylphosphoramide, 1,3-dimethyl-2-imidazolidinone, dimethyl sulfoxide or sulfolane.

It is advantageous to use 2 to 25 parts by weight of solvent per part by weight of the reactants. The amount ought to be sufficient to ensure a stirrable suspension. Moreover it is also possible to use the reactant nitrile of the formula (II) and/or (III) as a solvent at the same time, if it is liquid in the temperature range in which the reaction takes place.

In the process of the invention it is preferred to use an alcohol as solvent, especially a secondary or tertiary alcohol. Preferred tertiary alcohols are tert-butanol and tert-amyl alcohol.

It is also possible to use mixtures of the solvents, especially of the preferred secondary and tertiary alcohols with aromatic hydrocarbons, such as toluene or xylene, or with halogen-substituted benzene, such as chlorobenzene.

The process of the invention is carried out in the presence of a strong base. Suitable strong bases are, in particular, the alkali metals themselves, such as lithium, sodium or potassium, or alkali metal amides, such as lithium, sodium or potassium amide, or alkali metal hydrides, such as lithium, sodium or potassium hydride, or alkaline earth metal or alkali metal alkoxides, which derive in particular from primary, secondary or tertiary aliphatic alcohols having 1 to 10 carbon atoms, such as lithium, sodium or potassium methoxide, ethoxide, n-propoxide, isopropoxide, n-butoxide, sec-butoxide, tert-butoxide, 2-methyl-2-butoxide, 2-methyl-2-pentoxide, 3-methyl-3-pentoxide and 3-ethyl-3-pentoxide, for example. Mixtures of the stated bases can also be used.

In the process of the invention the strong base used preferably comprises alkali metal alkoxides, where the alkali metal is sodium or potassium in particular and the alkoxide derives preferably from a secondary or tertiary alcohol. Particularly preferred strong bases are therefore, for example, sodium or potassium isopropoxide, sec-butoxide, tert-butoxide and tert-amyloxide. The alkali metal alkoxides can also be prepared in situ by reacting the corresponding alcohol with the alkali metal, alkali metal hydride or alkali metal amide.

In the process of the invention the strong base can be used in an amount of 0.1 to 10 mol, preferably 1.9 to 5.0 mol, per mole of the reactant used in excess. Although stoichiometric amounts of base are sufficient in principle, an excess of base in many cases has an advantageous effect on the yield.

The inventive reaction of the succinic diester with the nitrites of the formula (II) or of the formula (III) is carried out in particular at a temperature of 60 to 200° C., preferably 80 to 140° C., under superatmospheric pressure if desired.

For the reaction the individual components can be added in any order, preferably at room temperature. It is also possible to introduce all of the components at a relatively low temperature and then to heat the mixture into the range of the reaction temperature. One preferred embodiment which generally has a particularly advantageous effect on the yield is to introduce the reactant nitrile together with the base and to meter in the succinic diester in the region of the reaction temperature. Another possibility is to meter in the succinic diester and the reactant nitrile simultaneously to the initial charge of base at reaction temperature. The process of the invention can be carried out batchwise or continuously. Particularly in the case of succinic diesters with lower alkyl radicals and in the case of alkoxides deriving from lower alcohols, such as methanol, ethanol, n-propanol, isopropanol or tert-butanol, for example, it may prove necessary to remove the lower alcohol, formed in the course of the reaction, continually from the reaction medium in order to obtain higher yields. If the solvent used is an alcohol and the base used is an alkoxide, then it may be advantageous to choose an alcohol and an alkoxide having the same alkyl moieties. It may be equally advantageous for the succinic diester to contain the same kind of alkyl groups as well.

The hydrolysis agent used to hydrolyze the reaction product may comprise water, one or more organic, protic solvents or one or more acids. Examples of suitable protic solvents include alcohols, preferably having 1 to 4 carbon atoms, such as methanol or ethanol. Suitable acids include organic acids, such as aliphatic or aromatic carboxylic or sulfonic acids, examples being formic acid, acetic acid, propionic acid, butyric acid, hexanic acid, oxalic acid, citric acid, benzoic acid, phenylacetic acid, benzenesulfonic acid or p-toluenesulfonic acid, and inorganic acids, examples being hydrochloric acid, sulfuric acid or phosphoric acid. For the hydrolysis it is preferred to use an organic acid, particularly an aliphatic carboxylic acid, such as acetic acid and formic acid. It is also possible to use water, organic protic solvent and/or acid in any combinations. The hydrolysis may also be carried out in the presence of organic aprotic solvents.

The hydrolysis may take place directly, by adding a hydrolysis agent to the reaction suspension, or indirectly, by adding the reaction suspension to the hydrolysis agent. The water, organic, protic solvent and acid hydrolysis agents can be added and/or introduced as an initial charge in any order and even as mixtures. The simultaneous addition of individual components to an initial charge is a further possibility: for example, acid and the reaction suspension can be added simultaneously to the initial charge of water and/or alcohol.

It may be advantageous to use a buffer during hydrolysis, such as a phosphate, acetate, citric acid or triethanolamine buffer, for example.

The temperature during the hydrolysis may be $-20°$ C. to $200°$ C., preferably $-5$ to $180°$ C., in particular 0 to $160°$ C., and the hydrolysis takes place under superatmospheric pressure if desired. Reaction suspension and hydrolysis agent may also differ in temperature. Hydrolysis may also take place, for example, by means of steam.

The total amount of hydrolysis agent is advantageously an at least stoichiometric amount relative to the base. For example, water and/or an organic, protic solvent can be used at between 0.5 and 50 parts by weight per part of the pigment formed. The acid is employed advantageously in a molar excess of from 0.1 to 10 times relative to base. Where a water-containing suspension is present after the hydrolysis, the pH may be situated in the alkaline, in the neutral or else in the acidic range.

Depending on the procedure the diketopyrrolopyrrole of the formula (I) is obtained in the course of the hydrolysis as a pigment, a finely divided prepigment or a coarsely crystalline crude pigment. Pigments present after the hydrolysis can be isolated in customary manner by filtration. Prior to the isolation of the pigment the solvent may be removed by distillation, where appropriate under reduced pressure, or else by steam distillation. This may even take place during the hydrolysis.

Prepigments and crude pigments must be further subjected to an aftertreatment. For this purpose the hydrolysis suspension can be used directly, or alternatively the pigment can be isolated first and then aftertreated.

The aftertreatment may comprise a thermal aftertreatment in water and/or organic solvent at any pH and at a temperature of 50 to $250°$ C., preferably from 80 to $190°$ C., under superatmospheric pressure if desired, for 10 minutes to 48 hours, preferably for 30 minutes to 8 hours, or a grinding operation, or a combination of these two operations.

Grinding may take place either by dry grinding or by wet grinding.

Mills suitable for dry grinding include all batch and continuous vibratory mills or roll mills, while suitable mills for wet grinding include all batch and continuous stirred ball mills, roll mills and vibratory mills and also kneading apparatus. Wet grinding takes place in water and/or organic solvent at any pH.

It is preferred to carry out wet grinding with a high energy input, as for example in a stirred ball mill with a power density of more than 1.0 kW per liter of milling space and a peripheral stirrer speed of more than 12 m/s. The hydrolysis agent or the reaction suspension may also be added in portions and sequentially, so that between the individual portions there may be an intermediate treatment, such as a period of prolonged stirring, for example, under elevated temperature if desired. For the aftertreatment it is preferred to use the hydrolysis suspension, without isolation of the diketopyrrolopyrrole beforehand.

In order to enhance the coloristic properties and to achieve certain performance effects it is possible to use auxiliaries such as surfactants, pigmentary and nonpigmentary dispersants, fillers, standardizers, resins, waxes, defoamers, antidust agents, extenders, shading colorants, preservatives, drying retarders, rheology control additives, wetting agents, antioxidants, UV absorbers, light stabilizers or a combination thereof.

Auxiliaries can be added at any desired point in time before, during or after the reaction, hydrolysis and/or aftertreatment, all at once or in two or more portions. The total amount of the added auxiliaries may amount to 0 to 40% by weight, preferably 1 to 30% by weight, more preferably 2.5 to 25% by weight, based on the diketopyrrolopyrrole pigment.

Suitable surfactants include anionic or anion-active, cationic or cation-active, and nonionic substances or mixtures of these agents. Preferred surfactants or surfactant mixtures are those which do not foam.

Examples of suitable anionic substances include fatty acid taurides, fatty acid N-methyltaurides, fatty acid isethionates, alkylphenylsulfonates, alkylnaphthalenesulfonates, alkylphenol polyglycol ether sulfates, fatty alcohol polyglycol ether sulfates, fatty acid amide polyglycol ether sulfates, alkylsulfosuccinamates, alkenylsuccinic monoesters, fatty alcohol polyglycol ether sulfosuccinates, alkanesulfonates, fatty acid glutamates, alkylsulfosuccinates, fatty acid sarcosides; fatty acids, examples being palmitic, stearic and oleic acid; soaps, examples being alkali metal salts of fatty acids, naphthenic acids and resin acids, such as abietic acid, alkali-soluble resins, examples being rosin-modified maleate resins and condensation products based on cyanuric chloride, taurine, N,N'-diethylaminopropylamine and p-phenylenediamine. Particular preference is given to resin soaps, i.e., alkali metal salts of resin acids.

Examples of suitable cationic substances include quaternary ammonium salts, fatty amine alkoxylates, alkoxylated polyamines, fatty amine polyglycol ethers, fatty amines, diamines and polyamines derived from fatty amines or fatty alcohols, and the alkoxylates of said amines, imidazolines derived from fatty acids, and salts of these cationic substances, such as acetates, for example.

Examples of suitable nonionic substances include amine oxides, fatty alcohol polyglycol ethers, fatty acid polyglycol esters, betaines, such as fatty acid amide N-propyl betaines, phosphoric esters of aliphatic and aromatic alcohols, fatty alcohols or fatty alcohol polyglycol ethers, fatty acid amide ethoxylates, fatty alcohol-alkylene oxide adducts and alkylphenol polyglycol ethers.

By nonpigmentary dispersants are meant substances which in structural terms are not derived from organic pigments by chemical modification. They are added as dispersants either during the actual preparation of pigments or else in many cases during the incorporation of the pigments into the application media to be colored: for example, during the preparation of paints or printing inks by dispersing of the pigments into the corresponding binders. They may be polymeric substances, such as polyolefins, polyesters, polyethers, polyamides, polyimines, polyacrylates, polyisocyanates, block copolymers thereof, copolymers of the corresponding monomers or polymers of one class modified with a few monomers of a different class. These polymeric substances carry polar anchor groups such as hydroxyl, amino, imino and ammonium groups, carboxylic acid and carboxylate groups, sulfonic acid and sulfonate groups or phosphonic acid and phosphonate groups, for example, and can also be modified with aromatic nonpigmentary substances. Nonpigmentary dispersants may additionally be aromatic substances modified chemically with functional groups but not derived from organic pigments. Nonpigmentary dispersants of this kind are known to the skilled worker and in some cases are available commercially (e.g., Solsperse®, Avecia; Disperbyk®, Byk, Efka®, Efka). A number of types will be mentioned below as representatives; however, it is possible in principle to use any desired other substances described, examples being condensation products of isocyanates and alcohols, diols or polyols, amino alcohols or diamines or polyamines, polymers of hydroxycarboxylic acids, copolymers of olefin monomers or vinyl monomers and ethylenically unsaturated carboxylic acids and esters, urethane-containing polymers of ethylenically unsaturated monomers, urethane-modified polyesters, condensation products based on cyanuric halides, polymers containing nitroxyl compounds, polyesteramides, modified polyamides, modified acrylic polymers, comb dispersants formed from polyesters and acrylic polymers, phosphoric esters, polymers derived from triazine, modified polyethers, or dispersants derived from aromatic, nonpigmentary substances. These base structures are in many cases modified further, by means for example of chemical reaction with further substances which carry functional groups, or by formation of salts.

By pigmentary dispersants are meant pigment dispersants which derive from an organic pigment as base structure and are prepared by chemical modification of said base structure; examples include saccharine-containing pigment dispersants, piperidyl-containing pigment dispersants, naphthalene- or perylene-derived pigment dispersants, pigment dispersants containing functional groups linked to the pigment base structure via a methylene group, pigment base structures modified chemically with polymers, pigment dispersants containing sulfo acid groups, sulfonamide groups or sulfo acid ester groups, pigment dispersants containing ether or thioether groups, or pigment dispersants containing carboxylic acid, carboxylic ester or carboxamide groups.

Mixtures of compounds of the formula (I) can also be prepared by joint hydrolysis of different reaction solutions prepared independently of one another, with or without mixing the reaction solutions beforehand, or else by joint reprecipitation of two or more compounds of the formula (I).

Asymmetrically substituted diketopyrrolopyrroles of the formula (I) can also be prepared by reacting not a nitrile with succinic diester but instead an ester of the formula (IV) or of the formula (V),

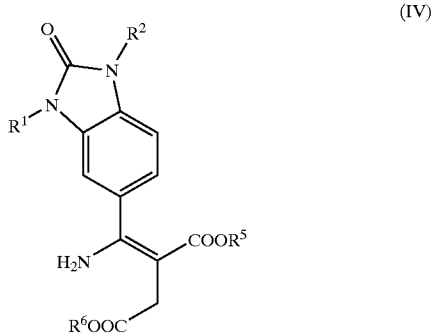

(IV)

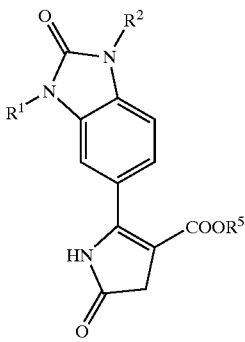

(V)

with a nitrile of the formula (III) in an organic solvent in the presence of a strong base with subsequent hydrolysis, $R^1$ and $R^2$ having the stated definition and $R^5$ and $R^6$ being an unsubstituted or substituted alkyl or aryl radical, preferably the ester radicals specified in connection with the succinic diesters.

This reaction can be carried out in analogy to the conditions described for the reaction of succinic diesters with nitrile.

The esters of the formula (IV) and of the formula (V) can be prepared in analogy to the processes disclosed in US-B1-6,207,697 or WO 00/34248.

The diketopyrrolopyrrole pigments of the invention can be employed as preferably aqueous presscakes, but generally comprise solids systems of free-flowing powderlike nature, or granules.

The diketopyrrolopyrrole pigments of the invention are notable particularly in coating materials for outstanding coloristic and rheological properties, and in particular for outstanding rheology, high transparency, effective gloss, high color strength, flawless overcoating fastnesses and very effective light fastness and weather fastness. They can be used in solventborne and in aqueous systems. In plastics and printing systems, too, they exhibit good properties and can therefore be used universally.

The diketopyrrolopyrrole pigments prepared in accordance with the invention can be used for pigmenting high molecular mass organic materials of natural or synthetic origin, such as plastics, resins, varnishes, paints or electrophotographic toners and developers, and also drawing, writing and printing inks, for example.

Examples of high molecular mass organic materials that can be pigmented with the stated pigments include cellulose ethers and cellulose esters, such as ethylcellulose, nitrocellulose, cellulose acetate or cellulose butyrate, natural resins or synthetic resins, such as addition-polymerization resins or condensation resins, examples being amino resins, especially urea-formaldehyde and melamine-formaldehyde resins, alkyd resins, acrylic resins, phenolic resins, polycarbonates, polyolefins, such as polystyrene, polyvinyl chloride, polyethylene, polypropylene, polyacrylonitrile, polyacrylic esters, polyamides, polyurethanes or polyesters, rubber, casein, silicone and silicone resins, individually or in mixtures.

It is irrelevant whether the aforementioned high molecular mass organic compounds are in the form of plastic masses, melts or in the form of spinning solutions, varnishes, paints or printing inks. Depending on the intended use it is found advantageous to utilize the pigments obtained in accordance with the invention in the form of a blend or in the form of preparations or dispersions. Based on the high molecular mass organic material to be pigmented, the pigments of the invention are used in an amount of from 0.05 to 30% by weight, preferably 0.1 to 15% by weight.

The pigments of the invention are also suitable for use as colorants in electrophotographic toners and developers, such as one- or two-component powder toners (also called one- or two-component developers), magnetic toners, liquid toners, polymerization toners and specialty toners, for example.

Typical toner binders are addition-polymerization resins, polyaddition resins and polycondensation resins, such as styrene, styrene-acrylate, styrene-butadiene, acrylate, polyester and phenol-epoxy resins, polysulfones, polyurethanes, individually or in combination, and also polyethylene and polypropylene, which may already include, or be modified subsequently with, further ingredient additions, such as charge control agents, waxes or flow assistants.

The pigments of the invention are further suited to use as colorants in powders and powder coating materials, particularly in triboelectrically or electrokinetically sprayable powder coating materials which are employed to coat the surfaces of articles made, for example, from metal, wood, plastic, glass, ceramic, concrete, textile material, paper or rubber.

Resins used as powder coating resins are typically epoxy resins, carboxyl- and hydroxyl-containing polyester resins, polyurethane resins and acrylic resins, together with customary curatives. Resin combinations also find use. Thus, for example, epoxy resins are frequently employed in combination with carboxyl- and hydroxyl-containing polyester resins. Typical curative components (depending on the resin system) are, for example, acid anhydrides, imidazoles and also dicyandiamide and its derivatives, blocked isocyanates, bisacylurethanes, phenolic and melamine resins, triglycidyl isocyanurates, oxazolines and dicarboxylic acids.

The pigments of the invention are also suitable for use as colorants in ink-jet inks, on both an aqueous and a nonaqueous basis, and also in those inks which operate in accordance with the hot-melt process.

Ink-jet inks generally contain a total of from 0.5 to 15% by weight, preferably 1.5 to 8% by weight, (calculated on a dry basis) of one or more of the compounds prepared in accordance with the invention.

Microemulsion inks are based on organic solvents, water and, if desired, an additional hydrotropic substance (interface mediator).

Microemulsion inks generally contain 0.5 to 15% by weight, preferably 1.5 to 8% by weight, of one of more of the compounds prepared in accordance with the invention, 5 to 99% by weight of water and 0.5 to 94.5% by weight of organic solvent and/or hydrotropic compound.

Solvent-based ink-jet inks contain preferably 0.5 to 15% by weight of one or more compounds prepared in accordance with the invention, 85 to 99.5% by weight of organic solvent and/or hydrotropic compounds.

Hot-melt inks are generally based on waxes, fatty acids, fatty alcohols or sulfonamides which are solid at room temperature and become liquid on heating, the preferred melting range being situated between about 60° C. and about 140° C. Hot-melt ink-jet inks are composed essentially, for example, of 20 to 90% by weight of waxes and 1 to 10% by weight of one or more of the compounds prepared in accordance with the invention. Additionally it is possible for them to contain from 0 to 20% by weight of an additional polymer (as "dye dissolver"), 0 to 5% by weight of dispersing assistant, 0 to 20% by weight of viscosity modifier, 0 to 20% by weight of plasticizer, 0 to 10% by weight of tack additive, 0 to 10% by weight of transparency stabilizer (which prevents, for example, crystallization of the waxes) and 0 to 2% by weight of antioxidant. Typical additives and auxiliaries are described for example in U.S. Pat. No. 5,560,760.

Additionally the pigments of the invention are also suitable for use as colorants for color filters, for both additive and subtractive color generation, and also for electronic inks.

To assess the properties of the pigments in the plastics field a selection was made, from among the multiplicity of known plastics, of plasticized polyvinyl chloride (PVC).

To assess the properties of the pigments in the printing sector a selection was made, from among the multiplicity of known printing systems, of a gravure printing system based on nitrocellulose (NC).

To assess the properties of the pigments in the coatings sector a selection was made, from among the multiplicity of known varnishes, of a high-solids acrylic resin stoving varnish based on a nonaqueous dispersion (HS), of an aqueous varnish based on polyurethane (PU), and of an alkyd-melamine resin varnish (AM) based on a medium-oil alkyd resin and on a butanol-etherified melamine resin.

The color strength and hue were determined in accordance with DIN 55986. The millbase rheology after dispersion was evaluated visually on the basis of the following five-point scale:
5 highly fluid
4 liquid
3 viscous
2 slightly set
1 set The overcoating fastness was determined in accordance with DIN 53221.

The viscosity was determined, following dilution of the millbase to the final pigment concentration, using the Rossmann viscospatula type 301 from Erichsen.

In the examples below, parts and percentages are by weight in each case.

EXAMPLE 1a

A four-necked flask is charged with 252.8 parts of tert-amyl alcohol, anhydrous. Following the introduction of 23 parts of sodium the mixture is stirred under reflux until the sodium has reacted. At 100° C. 58.6 parts of the nitrile of the formula (XX)

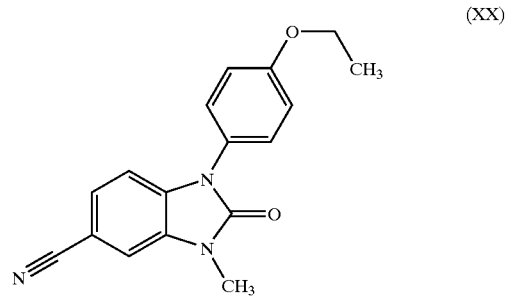

are introduced. Over the course of 2 hours 30.4 parts of diisopropyl succinate are added dropwise at 100° C. Then the mixture is stirred under reflux for 4 hours. After the reaction suspension has cooled to 80° C. it is poured into a mixture of 300 parts of water and 400 parts of methanol at 25° C. The hydrolysis suspension is stirred under reflux for 6.5 hours. After it is cooled to room temperature, 320 parts of methanol are added and stirred in, and then the suspension is filtered and the pigment is washed with methanol. The presscake is suspended in 1280 parts of methanol and stirred in, the suspension is filtered and the pigment is washed with methanol and water and dried at 80° C.

This gives 36.6 parts of diketopyrrolopyrrole pigment of the formula (XXI).

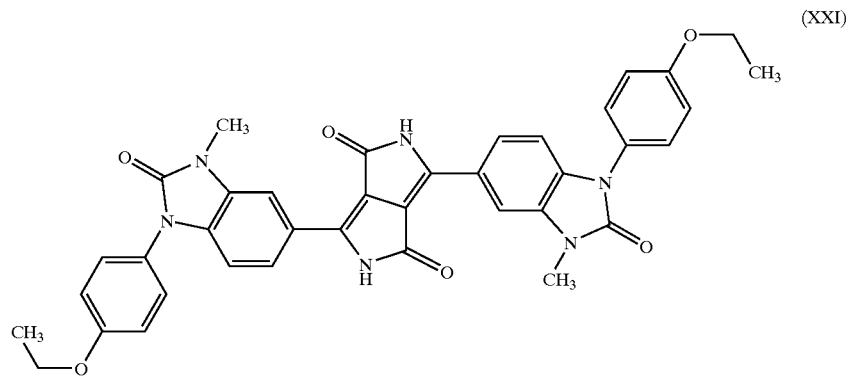

In the HS varnish the pigment provides transparent coatings with a strong, clean, orange hue and flawless overcoating fastness. The metallic finish is bright with a strong golden-yellow hue. In the PU varnish bright metallic finishes with a strong golden yellow hue are obtained; the rheology is very good and is rated 5.

EXAMPLE 1b (COMPARATIVE EXAMPLE)

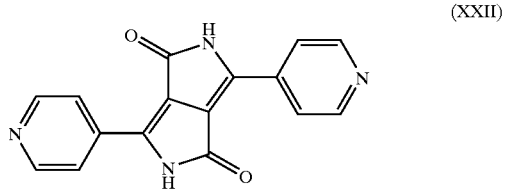

The diketopyrrolopyrrole of the formula (XXII) was prepared in accordance with EP 94911, example 12, and compared against the diketopyrrolopyrrole of the formula (XXI) prepared in accordance with example 1a. In the HS varnish the coatings are significantly more hiding and weaker in color, with a brownish red hue which is substantially more turbid. The weather fastness is also poorer. In the PU varnish the rheology is rated only at 2 to 3.

EXAMPLE 1c (COMPARATIVE EXAMPLE)

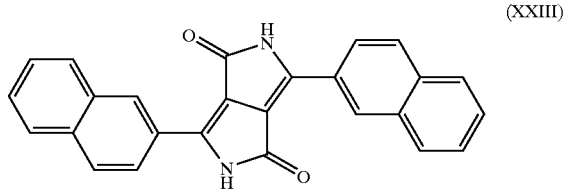

The diketopyrrolopyrrole of the formula (XXIII) was prepared in accordance with EP 94911, example 14, and compared against the diketopyrrolopyrrole of the formula (XXI) prepared according to example 1a. In the HS varnish the coatings are substantially more hiding and have a brownish violet hue which is substantially more turbid. The metallic coating is weak in color with a gray-brown hue. In the PU varnish as well a similar, markedly inferior coloristic quality is obtained.

EXAMPLE 2

A four-necked flask is charged with 189.6 parts of tert-amyl alcohol, anhydrous. Following the introduction of 17.3 parts of sodium the mixture is stirred under reflux until the sodium has reacted. At 100° C. 41.9 parts of the nitrile of the formula (XXIV)

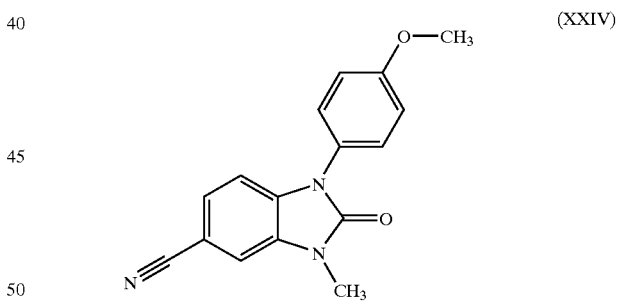

are introduced. Over the course of 2 hours 22.8 parts of diisopropyl succinate are added dropwise at 100° C. Then the mixture is stirred under reflux for 4 hours. After the reaction suspension has cooled to 80° C. it is poured into a mixture of 225 parts of water and 300 parts of methanol at 25° C. The hydrolysis suspension is stirred under reflux for 6.5 hours. After it is cooled to room temperature, 240 parts of methanol are added and stirred in, and then the suspension is filtered and the pigment is washed with methanol. The presscake is suspended in 960 parts of methanol and stirred in, the suspension is filtered and the pigment is washed with methanol and water and dried at 80° C.

This gives 26.8 parts of diketopyrrolopyrrole pigment of the formula (XXV).

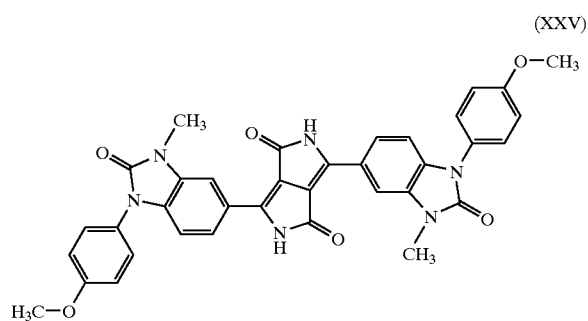

(XXV)

In the HS varnish the pigment provides transparent coatings with a clean, orange hue and flawless overcoating fastness.

EXAMPLE 3

A four-necked flask is charged with 189.6 parts of tert-amyl alcohol, anhydrous. Following the introduction of 17.3 parts of sodium the mixture is stirred under reflux until the sodium has reacted. At 100° C. 5 parts of the nitrile of the formula (XXIV) and 38.6 parts of the nitrile of the formula (XX) are introduced. In 2 hours 22.8 parts of diisopropyl succinate are added dropwise at 100° C. Then the mixture is stirred under reflux for 4 hours. After the reaction suspension has cooled to 80° C. it is poured into a mixture of 225 parts of water and 300 parts of methanol at 25° C. The hydrolysis suspension is stirred under reflux for 2 hours. After it has cooled to room temperature 240 parts of methanol are added and stirred in and then the suspension is filtered and the pigment is washed with methanol. The presscake is suspended in 960 parts of methanol and stirred in, the suspension is filtered and the pigment is washed with methanol and water and dried at 80° C. This gives 25.9 parts of diketopyrrolopyrrole pigment composed of a mixture of pigments of the formula (XXI), (XXV) and (XXVI).

In the PU varnish the pigment produces transparent coatings with a claret hue and flawless overcoating fastness. In contrast to this a commercially customary pigment P.R.255, prepared in accordance with the process disclosed in EP 94911, exhibits an inadequate overcoating fastness in the PU varnish.

EXAMPLE 4

A four-necked flask is charged with 176 parts of tert-amyl alcohol, anhydrous. Following the introduction of 13.8 parts of sodium the mixture is stirred under reflux until the sodium has reacted. At 100° C. 39.5 parts of the nitrile of the formula (XXVII)

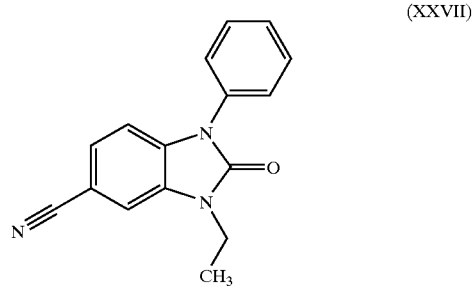

(XXVII)

are introduced. Over the course of 5 hours at 100° C. 22.7 parts of diisopropyl succinate are added dropwise. Then the mixture is stirred under reflux for 1 hour. After the reaction suspension has cooled to 80° C. it is poured into 430 parts of water at 40° C. The hydrolysis suspension is stirred under reflux for 4.5 hours. After it has cooled to room temperature 670 parts of methanol are added and stirred in and then the suspension is filtered and the pigment is washed with methanol and water and dried at 80° C.

This gives 32.8 parts of diketopyrrolopyrrole pigment of the formula (XXVIII).

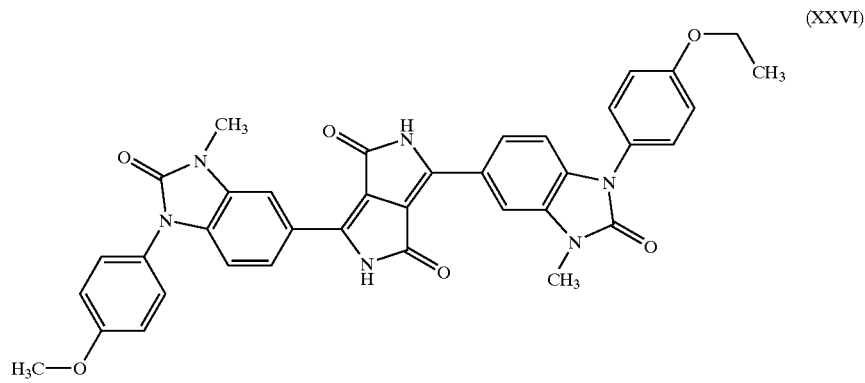

(XXVI)

(XXVIII)

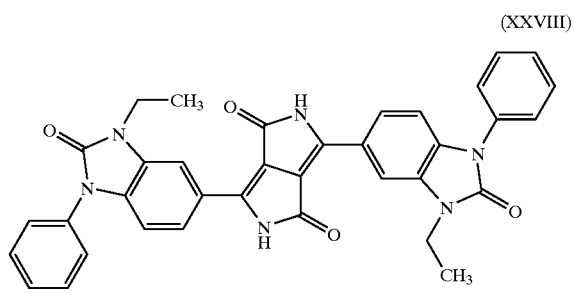

In the AM varnish the pigment produces opaque coatings with a strong yellowish-red hue and flawless overcoating fastness; the viscosity amounts to 3 sec. In PVC, strong colorations with an orange hue, and in the NC print strong colorations with a yellowish-red hue, are obtained.

What is claimed is:

1. A diketopyrrolopyrrole of the formula (I)

(I)

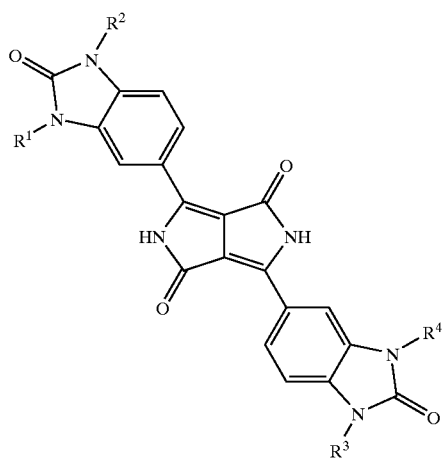

wherein

R$^1$, R$^2$, R$^3$ and R$^4$ independently of one another are a C$_1$–C$_4$ alkyl radical or a substituted or unsubstituted phenyl radical, wherein the substituted phenyl radical is substituted by 1, 2, 3 or 4 substituents selected from the group consisting of C$_1$–C$_4$ alkyl, C$_1$–C$_4$ alkoxy, CN, F, Cl, Br, NO$_2$, CF$_3$, S—C$_1$–C$_4$ alkyl, phenyl and (C$_1$–C$_2$) alkylenephenyl, with the proviso that at least one of the radicals, R$^1$, R$^2$, R$^3$, or R$^4$, is a substituted or unsubstituted phenyl radical.

2. A diketopyrrolopyrrole as claimed in claim 1, wherein the radicals R$^1$ and R$^4$ are identical and the radicals R$^2$ and R$^3$ are identical.

3. A diketopyrrolopyrrole as claimed in claim 1, wherein the radicals R$^1$, R$^2$, R$^3$ and R$^4$ independently of one another are methyl, ethyl, phenyl or phenyl substituted by 1 or 2 substituents selected from the group consisting of methyl, ethyl, methoxy, ethoxy, CN, F, Cl, S-methyl, phenyl and benzyl.

4. A diketopyrrolopyrrole as claimed in claim 1, wherein R$^1$ and R$^4$ are each a methyl or ethyl group and R$^2$ and R$^3$ are each an identical phenyl radical which is unsubstituted or substituted by 1 or 2 substituents selected from the group consisting of methyl, ethyl, methoxy, ethoxy, F, Cl, NO$_2$, CF$_3$, phenyl and benzyl.

5. A mixture of two or more diketopyrrolopyrroles as claimed in claim 1.

6. A process for preparing a diketopyrrolopyrrole as claimed in claim 1, comprising the steps of reacting a succinic diester with a nitrile of the formula (II) (III), or with a mixture of 2, 3 or 4 different nitriles of the formula (II) or (III), (II)

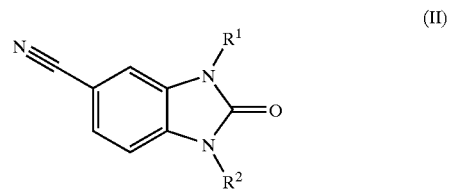

(III)

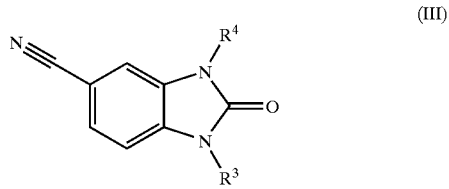

in an organic solvent in the presence of a strong base and subsequently hydrolyzing.

7. A process for preparing a diketopyrrolopyrrole of the formula (I) as claimed in claim 1, comprising the steps of reacting an ester of the formulae (IV) or (V)

(IV)

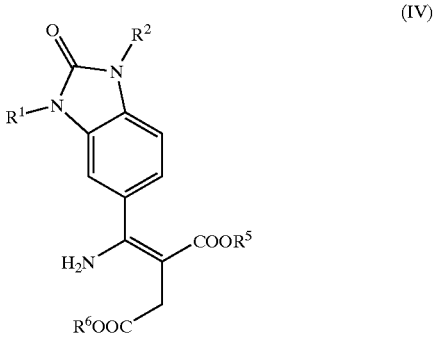

(V)

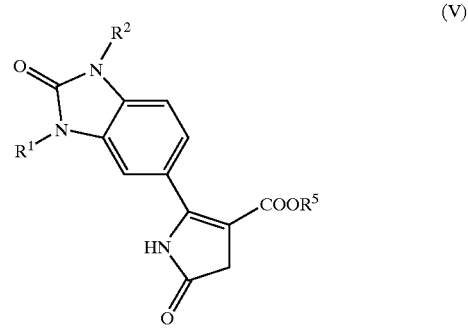

in which R$^5$ and R$^6$ are an unsubstituted or substituted alkyl or aryl radical, with a nitrile of the formula (III)

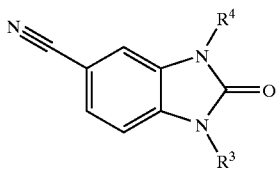

in an organic solvent in the presence of a strong base and subsequently hydrolyzing.

8. A pigmented high molecular mass organic material of natural or synthetic origin pigmented with at least one diketopyrrolopyrrole as claimed in claim 1.

9. The pigmented high molecular mass organic material as claimed in claim 8, wherein the pigmented high molecular mass material is an ink-jet ink.

10. A compound of the formula (IV)

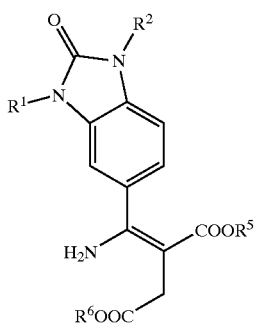

wherein $R^5$ and $R^6$ are an unsubstituted or substituted alkyl or aryl radical and $R^1$ and $R^2$ independently of one another are a $C_1$–$C_4$ alkyl radical or a substituted or substituted phenyl radical, wherein the unsubstituted phenyl radical is substituted by 1, 2, 3 or 4 substituents selected from the group consisting of $C_1$–$C_4$ alkyl, $C_1$–$C_4$ alkoxy, CN, F, Cl, Br, $NO_2$, $CF_3$, S—$C_1$–$C_4$ alkyl, phenyl and ($C_1$–$C_2$)alkylenephenyl, with the proviso that at least one of the radicals, $R^1$ and $R^2$ is a substituted or unsubstituted phenyl radical.

11. The pigmented high molecular mass organic material as claimed in claim 8, wherein the pigmented high molecular mass material is selected from the group consisting of plastics, resins, varnishes, paints, electrophotographic toners, electrophotographic developers, color filters, drawing inks, writing inks and printing inks.

12. A compound of the formula (V)

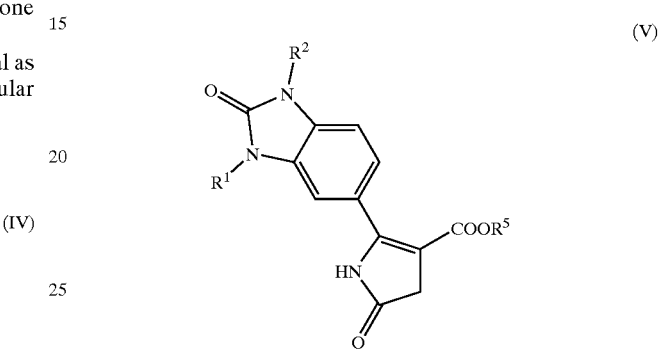

wherein $R^5$ is an unsubstituted or substituted alkyl or aryl radical and $R^1$ and $R^2$ independently of one another are a $C_1$–$C_4$ alkyl radical or a substituted or substituted phenyl radical, wherein the unsubstituted phenyl radical is substituted by 1, 2, 3 or 4 substituents selected from the group consisting of $C_1$–$C_4$ alkyl, $C_1$–$C_4$ alkoxy, CN, F, Cl, Br, $NO_2$, $CF_3$, S—$C_1$–$C_4$ alkyl, phenyl and ($C_1$–$C_2$)alkylenephenyl, with the proviso that at least one of the radicals, $R^1$ and $R^2$ is a substituted or unsubstituted phenyl radical.

* * * * *